United States Patent [19]
Hamedi

[11] Patent Number: 5,456,709
[45] Date of Patent: Oct. 10, 1995

[54] INTERLOCKING ELECTRODE CARRYING BODY CAVITY INSERT FOR TREATING MEDICAL CONDITIONS

[75] Inventor: Hassan Hamedi, Milwaukee, Wis.

[73] Assignee: Myo Kinetic Systems, Inc., Menomonee Falls, Wis.

[21] Appl. No.: 214,349

[22] Filed: Mar. 16, 1994

[51] Int. Cl.$^6$ ..................................................... A61N 1/05
[52] U.S. Cl. .......................................... 607/138; 607/148
[58] Field of Search ........................... 607/138, 148, 607/116, 119, 122, 127, 124, 133, 134, 135, 136; 128/639, 642, 733, 738; 601/15

[56] References Cited

U.S. PATENT DOCUMENTS

| | | | |
|---|---|---|---|
| 1,149,971 | 8/1915 | Wogone | 607/138 |
| 1,195,933 | 8/1916 | Wogone | 607/128 |
| 3,800,800 | 4/1974 | Garbe et al. | 607/138 |
| 3,866,613 | 2/1975 | Kenny et al. | 128/408 |
| 4,785,828 | 11/1988 | Maurer | 128/788 |
| 4,881,526 | 11/1989 | Johnson et al. | 601/15 |
| 4,909,263 | 3/1990 | Norris | 607/138 |
| 5,010,895 | 4/1991 | Maurer et al. | 607/138 |
| 5,046,511 | 9/1991 | Maurer et al. | 607/138 |
| 5,199,443 | 4/1993 | Maurer et al. | 607/138 |

FOREIGN PATENT DOCUMENTS

| | | | |
|---|---|---|---|
| 2547203 | 6/1983 | France | 607/138 |
| 3518317 | 5/1985 | Germany | 607/138 |

Primary Examiner—Lee S. Cohen
Assistant Examiner—Brian M. Green
Attorney, Agent, or Firm—Quarles & Brady

[57] ABSTRACT

A body cavity insert for transmitting electrical energy between a body cavity wall and an electrical device has conductive and nonconductive segments which are interconnected to form the whole body cavity insert. The segments are connected by snap fit, threads or other interference or friction fits. The conductive segments may comprise a conductive polymer outer layer and an inner metal layer to which electrical leads may be easily be conductively and mechanically attached.

5 Claims, 4 Drawing Sheets

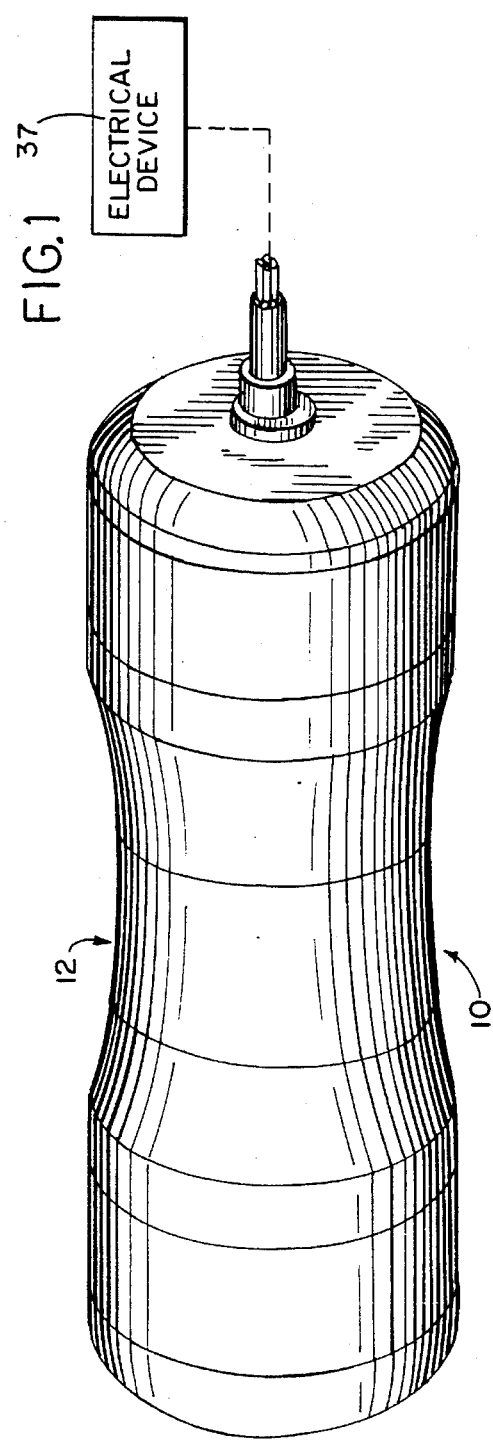
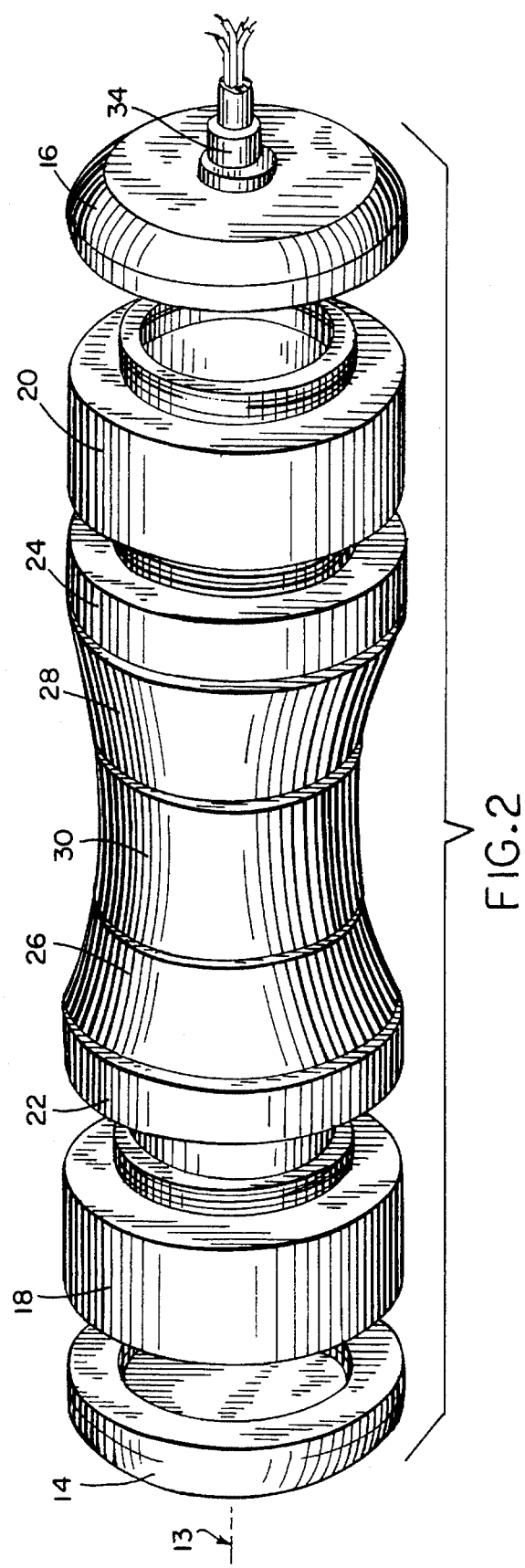

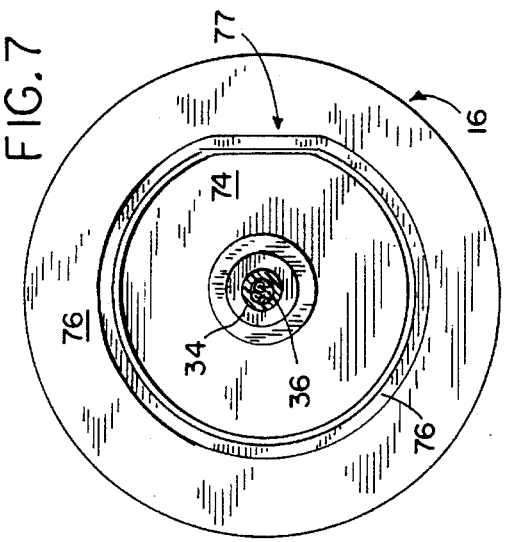
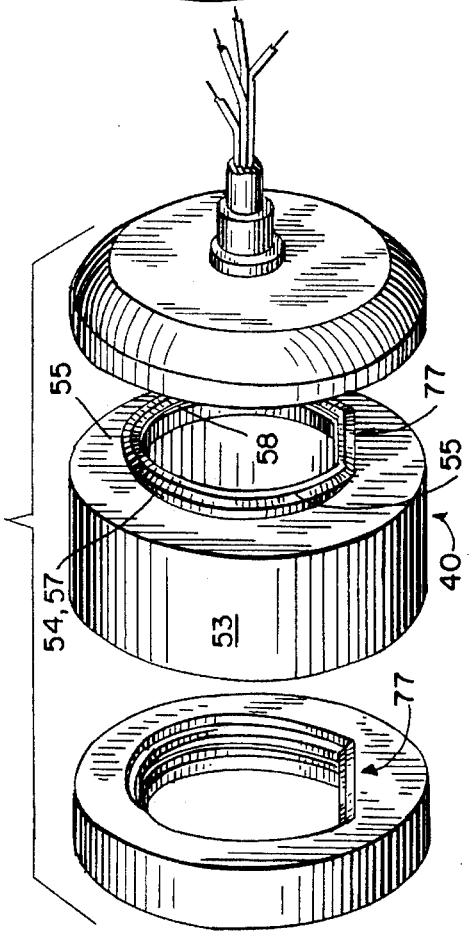
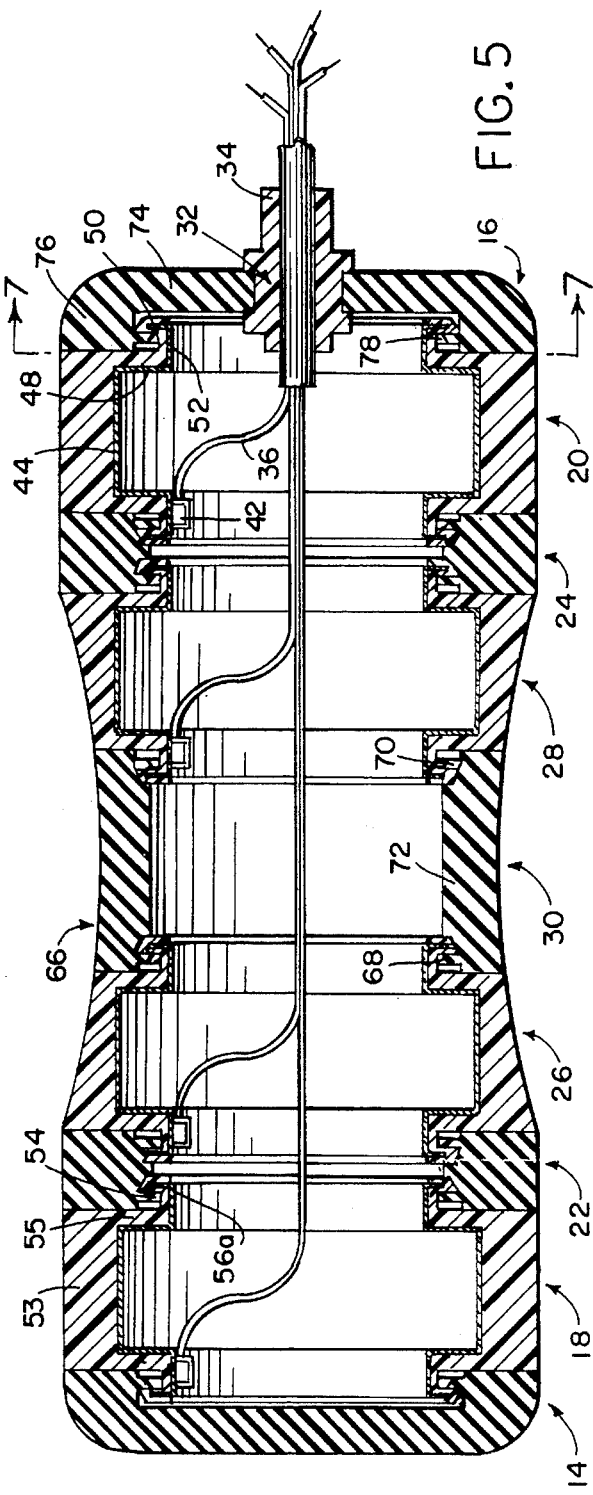

INTERLOCKING ELECTRODE CARRYING BODY CAVITY INSERT FOR TREATING MEDICAL CONDITIONS

BACKGROUND OF THE INVENTION

1. Field of the Invention

The field of the invention is that of electrode-carrying body cavity inserts used in medical treatments.

Although the invention is generally described herein in terms of an intra-vaginal embodiment for treating urinary incontinence in women, it is not limited to that. For example, it may be employed intra-vaginally to treat other conditions in which electrical transmission to or from a body cavity may be found beneficial. It may also be found useful to be employed intra-anally in men or women to treat incontinence or other conditions.

2. Description of the Prior Art

It is known to treat female urinary incontinence with electrical stimulation applied to the walls of the vagina via electrodes carried by a probe inserted into the vagina. See, for example, Eriksen and Eik-Ness, Long-Term Electrostimulation of the Pelvic Floor: Primary Therapy in Female Stress Incontinence, 44 Urology International 90–95 (1989); Fall, Does Electrostimulation Cure Urinary Incontinence, 131 The Journal of Urology 664–667 (1984).

By activating pudendal nerve branches, such stimulation causes contraction of the muscles of the pelvic floor. Repeated sessions of such stimulation can strengthen and retrain those muscles and thereby alleviate stress incontinence in which urine passes with the onset of abdominal pressure which may result from stressed or quick activities, including sneezing and jumping. Repeated sessions of such electrical stimulation can also alleviate urge incontinence, which results from involuntary bladder contractions; the electrical stimulation apparently inhibits reflex actions of the various pelvic nerves which are responsible for bladder control.

The electrical stimulation which is supplied consists of a train of pulses. It has been found that the optimum combination of frequency, amplitude and other characteristics of these pulses differs as between individual patients and in one patient between stress incontinence therapy and urge incontinence therapy. Accordingly, vaginal inserts have been provided with two pairs of electrodes which have been powered by a pulse generator having two channels. See, e.g., U.S. Pat. No. 4,881,526 issued to Johnson and Maurer on Nov. 2, 1989. The pulse generator may be designed to allow the physician to program individualized pulse train patterns.

An electrode-carrying insert has been used in electromyographical biofeedback treatments. In those usages, the electrodes on the insert transmit electrical signals in the other direction—i.e., the electrodes detect from the vaginal or rectal wall the minute electrical impulses resulting from muscle activity and transmit those impulses to electrical components which display them to the patient. The patient utilizes the display in a biofeedback process to develop conscious and willful control over his or her muscles. U.S. Pat. No. 4,396,019, Perry, Jr., Aug. 2, 1983.

One type of intravaginal electrode-carrying insert is relatively rigid or semi-rigid and carries electrodes in the form of rings or bands around the insert. The outer surface of the insert (including both the conductive rings and the nonconductive rings which insulate the conducting rings from each other) is ideally made from a biocompatible polymer. However, effectively connecting electrical leads to conductive polymer has proven to be difficult.

Prior art body cavity inserts pose other manufacturing problems as well. Polymer inserts with alternating conductive and nonconductive rings have been made by molding conductive bands into the surface of a nonconductive polymer-carrier or by fastening conductive bands to the exterior surface of the carrier by adhesives. This manufacturing process has proven to be difficult and expensive.

In addition, manufacturing inserts to accommodate different sizes of patients may be expensive.

SUMMARY OF THE INVENTION

The objects of the invention are to provide a rigid or semi-rigid electrode-carrying body cavity insert: (a) which provides an effective and convenient means of electrical connection between the electrical leads and the conductive electrodes which are in contact with the body cavity; (b) which facilitates manufacture of electrodes in different sizes; and (c) which can be manufactured economically.

In one aspect, the body cavity insert for transmitting electrical energy between a body cavity wall and an electrical device includes first and second conductive members having first and second connector elements respectively, and a nonconductive member having third and fourth connector elements. First and second leads are in conductive communication with the first and second conductive members respectively, and are also disposed to be in conductive communication with the electrical device. The first connector element and the third connector element are adapted to mate and thereby mechanically connect the first conductive member to the nonconductive member, and the second connector element and the fourth connector element are adapted to mate and thereby mechanically connect the second conductive member to the nonconductive member. In a particular aspect, either the first connector element or the third connector element comprises a projection and the other comprises a groove, or in another aspect they are threaded, and they may mate in a friction fit or in an interference fit.

In another aspect, the first conductive member comprises a conductive polymer layer having an outer surface adapted to adjoin the body cavity wall and an inner surface which substantially and conductively adjoins a layer of metal, the first lead being connected to the metal layer. In that aspect, the conductive polymer layer and the metal layer may have a fifth and a sixth connector element respectively which are adapted to mate in a projection/groove fit, by threads, by friction or by interference and thereby hold the conductive polymer layer and metal layer in substantial mechanical and electrical contact. The first lead may be crimped to a projection extending from the metal layer.

The invention provides effective electrical connection between the electrical leads and the electrodes which contact the body cavity wall by providing an underlying metal base for each electrode band; connecting the electrical lead to the metal base is easier than connecting it to conductive polymer. The invention facilitates economical manufacture by providing for the separate manufacture of conductive and nonconductive segments which can be assembled by friction fit, threaded fit or other methods which are simpler than the methods known in the prior art. These segments can be made in several lengths, the combination of which can provide inserts of varying lengths.

Other objects and advantages of the invention will be apparent from the description which follows.

BRIEF DESCRIPTION OF THE DRAWINGS

FIG. 1 is a perspective view of an assembled body cavity insert;

FIG. 2 is an exploded view showing the separate parts of the body cavity insert of FIG. 1;

FIG. 5 is a cross sectional view of an embodiment employing a different form of interconnection;

FIG. 6 is an enlarged exploded view illustrating the interconnective elements of the embodiment of FIG. 5;

FIG. 7 is a cross sectional view taken on line 7—7 of FIG. 5;

DETAILED DESCRIPTION OF THE DRAWINGS

Figure 4:
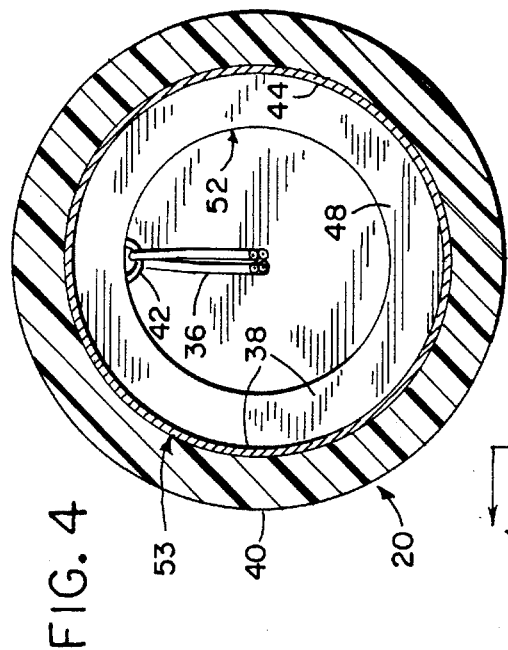
FIG. 4 is a cross sectional view taken on line 4—4 of FIG. 3.
Figure 8:
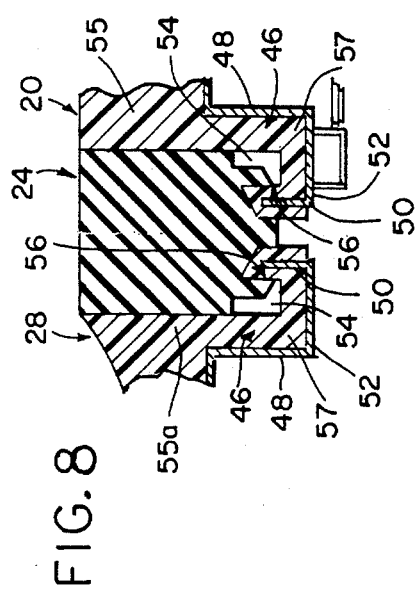
FIG. 8 is an enlarged cross sectional view of the interconnection of elements in the embodiment of FIG. 5.

As shown in FIG. 1, body cavity insert 10 is an elongated, generally cylindrical, hollow body with a narrowed central waist portion 12. As illustrated in FIG. 2, it is assembled by interlocking (as will be described below) the following members along a longitudinal axis 13: nonconductive end caps 14 and 16, outboard conductive segments 18 and 20, intermediate nonconductive segments 22 and 24, inboard conductive segments 26 and 28, and middle nonconductive segment 30. The end cap 16 has a central opening 32 through which is inserted a cylindrical lead channel 34. Four electrical leads 36 coming from an electrical device 37 pass through the lead channel 34 and are connected (as will be described below) to the conductive segments 18, 20, 26 and 28. All of the segments may be made substantially of a rigid or semi-rigid polymer. The conductive segments 18, 20, 26 and 28 are made conductive by adding carbon, copper, silver or other metals to the polymer.

As seen best in FIG. 4, in one embodiment the conductive segments 18, 20, 26 and 28 each comprise three parts: a metal base 38, a conductive outer ring 40 and a receptacle or other lead connection means 42.

Figure 9:
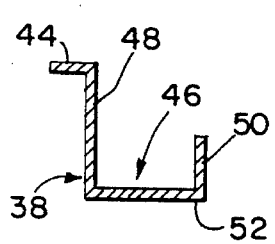
FIGS. 9–11 are enlarged cross sectional views of the interconnective elements of the embodiment of FIG. 5.

As seen especially in FIG. 9, in a preferred embodiment, each metal base 38 has a cylindrical double-pulley-like shape defined by a cylindrical wall (base cylindrical wall 44) on each edge of which is an outwardly opening groove space (base groove space 46) defined by a radially inward extending wall (base inboard radial wall 48), an outwardly extending radial wall (base outboard radial wall 50) and a groove floor (base groove floor 52) between them. ("Inwardly" means toward the longitudinal axis 13, and "outwardly" means away from it.) The metal base 38 could, of course have other configurations as well.

Figure 10:
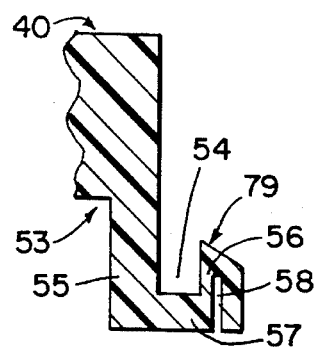

In one embodiment, shown in FIGS. 5–8 and 10, 11, and best seen in FIG. 10, each conductive outer ring 40 has similar double-pulley-like shape sized so that it can adjoin the outer surface of the metal base 38. It has a cylindrical wall (or in the case of the conductive segments 26, 28, a curved conical wall) (ring cylindrical wall 53) on each edge of which is an outwardly opening groove space (ring groove space 54) defined by a radially inwardly extending wall (ring inboard radial wall 55), an outwardly extending radial wall (ring outboard radial wall 56) and a groove floor (ring groove floor 57) between them. The ring outboard radial wall 56 has a slot 58 of sufficient width to accept the base outboard radial wall 50. The conductive outer ring 40 could be made in other configurations as well.

The metal base 38 and the conductive outer ring 40 can be co-joined as part of the process of molding the ring 40. If that is done, the double pulley shape of the metal base 38 may be eliminated so that metal base 38 would then be a simple tube. For example, the metal base 38 may be placed on a mandrel or anvil in the mold and the ring 40 may be molded around it. Adhesive may be used to adhere the base 38 to the ring 40. Alternatively, the base 38 may be sandwiched between an inner layer of non-conductive material and the ring 40. Etching the outer surface of metal base 38 enhances the connection between it and the conductive outer ring 40. The lead 36 may be attached to the metal base 38 prior to this molding process.

Alternatively, metal base 38 and the ring 40 can be snapped together so that the base outboard radial walls 50 are engaged in slots 58 of the ring 40. This process can be facilitated by making the base cylindrical wall 44 circumferentially discontinuous so that it can be made to overlap itself, thereby temporarily reducing the diameter of base 38.

However the parts are put together, the result is a single base 38/ring 40 assembly having an inner metal layer and an outer conductive polymer layer. The base 38/ring 40 assembly comprises each of conductive segments 18, 20, 26, 28. The outer surface of the metal base 38 can be etched, primed or otherwise treated to enhance electrical conductivity between it and the conductive outer ring 40.

The male/female interconnection of metal base 38 and conductive outer ring 40 could, of course, be reversed.

Figure 12:
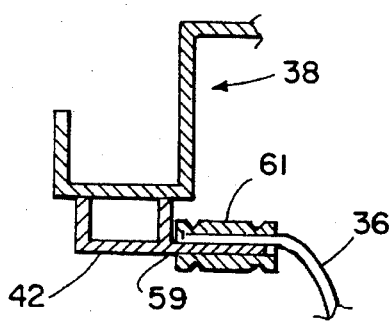
FIG. 12 is an enlarged cross sectional view of a crimp connection.

The lead receptacle 42 is in electrically conductive communication with metal base 38 and may be an integral part of it. The lead receptacle 42 may be a solder cup, a clamp, a hook, a jack, a crimping structure, or other means for mechanically and electrically connecting the lead 36 to the metal base 38. FIG. 12 illustrates one particular form in which a lip 59 projects from lead receptacle 42. A butt splice 61 is crimped onto lip 59 and lead 36 to effect a mechanical and an electrical connection. The connecting element of lead receptacle 42 may be etched or otherwise treated to provide improved electrical and mechanical bonding.

Figure 13:
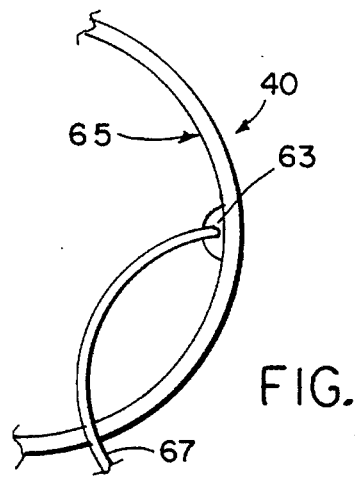
FIG. 13 is an enlarged schematic view of a conductive ring with a conductive mound.
Figure 14:
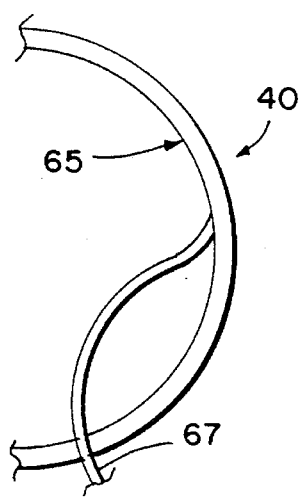
FIG. 14 is an enlarged schematic view of a conductive ring with a conductive tail.

In another aspect of the invention, the metal base 38 is dispensed with. Instead, as shown in FIG. 13, a nipple or mound 63 of conductive polymer or other material is formed on the inner surface 65 of conductive ring 40. A conductor 67 is made to pierce the mound, and may be further secured to it by adhesive, winding, tying or other means. Alternatively, as shown in FIG. 14 the conductor 67 may be an electrically conductive polymer strap or tail extruded from the conductive ring 40 in the course of molding it. A lead 36 may be joined to the conductor 67 by crimping, soldering, winding or other means.

In one embodiment, shown in FIGS. 5–8 and 10, 11, the intermediate nonconductive segments 22, 24 are donut-like members whose inner surface is modulated to form three lugs—the outboards lugs 60 and 62 and the inboard lug 64.

As shown in FIG. 5, the middle nonconductive segment 30 is wider than the intermediate nonconductive segments 22, 24, and has a concave outer surface 66. As with the intermediate nonconductive segments 22, 24, the middle nonconductive segment 30 has three inner surface lugs—the outboard lugs 68 and 70 and the inboard lug 72 which is elongated in comparison with inboard lug 64 to reflect the greater width of middle nonconductive ring 30.

In the embodiment shown in FIGS. 5–8 and 10, 11, the nonconductive end caps 14, 16 are dish-shaped and comprise a floor 74 from which projects a circumferential wall 76. (FIG. 5) A lug 78 projects inwardly from wall 76. The floor 74 of end cap 16 has an access hole for the electrical leads 36.

Each of the conductive and nonconductive segments may be formed with a flat surface 77 on its interconnection structure to prevent the elements from rotating with respect to each other.

Figure 11:
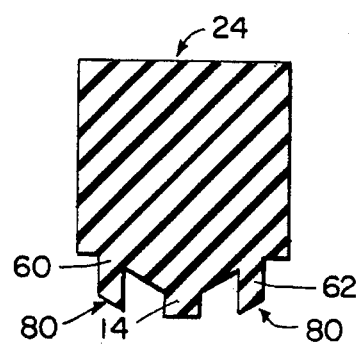

Each conductive segment (18, 20, 26, 28) is joined on each of its sides to a nonconductive segment (14, 16, 22, 24, 30). To do that, an outboard lug (60, 62, 68, 70, or 78) of a nonconductive segment is pressed against the ring outboard radial wall 56 and snapped into ring groove space 54. FIGS. 10 and 11 illustrate that the edge 79 of ring outboard radial wall 56 and the edge 80 of the outboard lug (60, 62, 68, 70, or 78) are formed on a diagonal to facilitate accomplishing the snap fit.

This procedure is followed until the entire insert 10 is assembled as shown in FIG. 1, whereby the segments are held together in fixed relation to each other by friction and interference forces.

Figure 3:
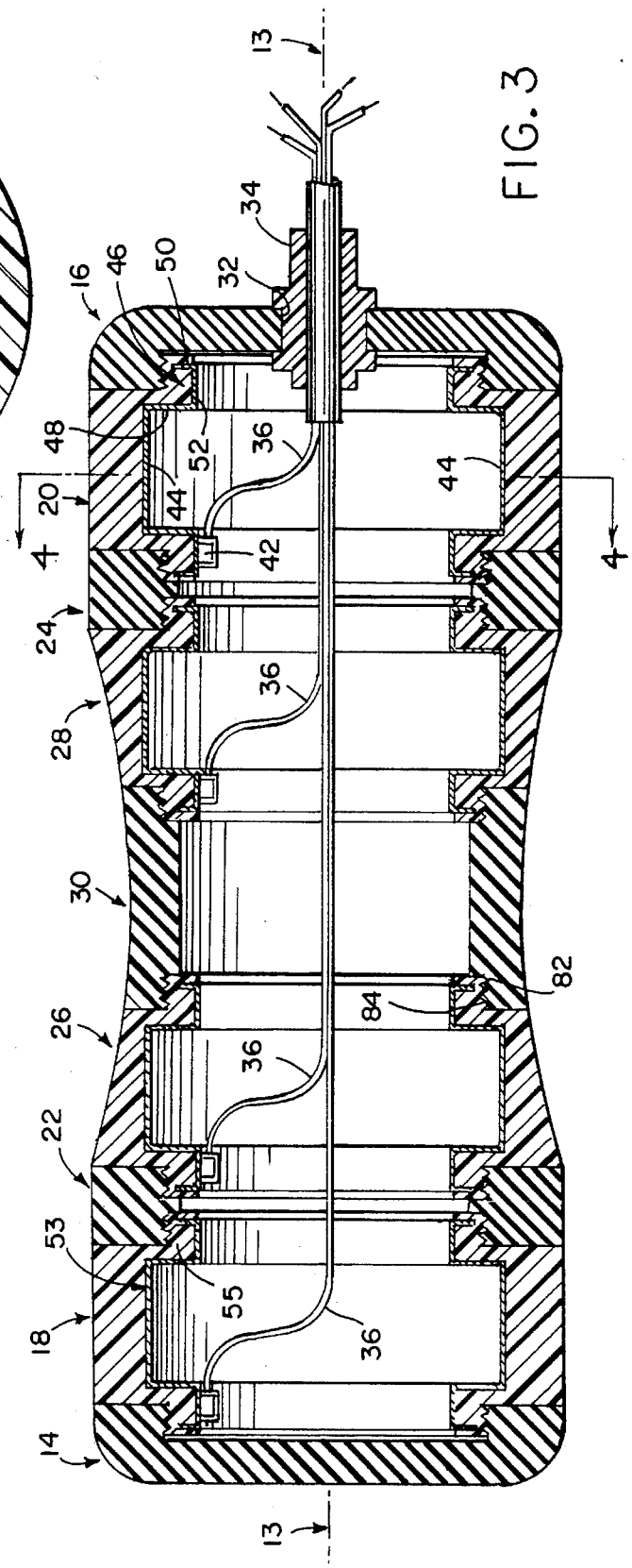
FIG. 3 is a cross sectional view of an embodiment employing threaded interconnection.

FIG. 3 illustrates an alternate structure for interconnecting the segments of insert 10. In that embodiment, the various components are the same as just described except that the interlocking of the conductive segments (18, 20, 26, 28) with the non-conductive segments (14, 16, 22, 24, 30) is accomplished by threaded connections rather than the lug-in-groove snap fit just described. The lugs (60, 62, 64, 68, 70, 78) of the nonconductive segments (14, 16, 22, 24, 30) have been replaced by threads 82, and, on the conductive segments (18, 20, 26, 28) the ring outboard radial wall 56 has been replaced by threads 84 on the ring groove floor 57. The insert 10 is assembled by the threadably fastening conductive segments to nonconductive segments. Spiralock Threads made by Detroit Tool Industries, Madison Heights, Mich. 48071-0629, may be used advantageously.

A single body cavity insert 10 may include both types of interconnecting structures shown in FIGS. 3 and 5.

A medical grade adhesive may be used to secure the interconnecting structures of the embodiments of FIGS. 3 or 5. The adhesive also acts as a moisture seal.

Figure 15:
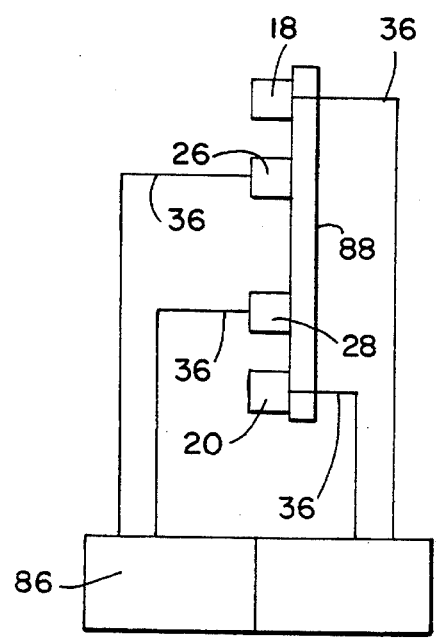
FIG. 15 is a schematic representation of electrical circuits with which the insert may be employed.

FIG. 15 schematically illustrates the electrical circuits formed with the conductive segments (or electrodes) 18, 20, 26, 28 when the device is used in electro-therapy. In one embodiment, the electrical device 37 is a pulse generator 86 having two channels for producing patterns of electrical pulses. Various parameters of the electrical signals may be controlled in order to customize a treatment regime for a particular patient. Examples of pulse generators are found in these U.S. Pat. Nos. 4,515,167, Hochman, May 7, 1985; 4,785,828, Maurer, Nov. 22, 1988; and 4,881,526, Johnson and Maurer, Nov. 21, 1989. The output connections of one channel are electrically connected respectively to electrodes 18 and 20, which are positioned primarily to treat stress incontinency. The contact of electrodes 18 and 20 with selected portions of the vaginal wall 88 completes the circuit between electrodes 18, 20 and one channel of the pulse generator 86. The second channel of the pulse generator 86 is similarly connected to vaginal wall 88 via electrodes 26 and 28 which are positioned primarily to treat urge incontinency.

In electromyography feedback usages, the electrical device 37 typically amplifies the electrical signals received from the body cavity wall and transforms it into an auditory, tactile or visual display for immediate reception by the patient. See, for example, U.S. Pat. No. 4,396,019, Perry, Jr., Aug. 2, 1983. The insert may include a ground or reference electrode.

As used herein, the term "electrical device" includes devices which transmit electrical energy and devices which receive and process electrical energy. The invention may transmit electrical energy from the electrical device to the body cavity wall or vice versa.

Although the preferred embodiments of the invention have been described above, the invention claimed is not so restricted. For example, metal base 38 could be eliminated. In that case, the lead 36 could be attached directly to the conductive outer ring 40 by adhesive, crimping to a "tail" of polymer extending from the outer ring 40, or by other means. In another alternative, the metal base 38 would be employed, and it would be modified in structure so that it could be relied upon to provide the snap fit similar to that provided by the embodiment of FIG. 5; in that case, the groove structure of the conductive outer ring 40 (as particularly shown in FIG. 10) could be eliminated or simplified. Further, the body cavity insert 10 need not have the narrowed waist portions shown in FIGS. 3 and 5. It may have no waist portion, or the waist portion might be located in a different portion of the insert 10. For example, it may be located adjacent the end cap 16 if, for example, the sphincter muscle is to be addressed. Alternatively, the end cap 16 may itself include a waist portion in an insert 10 intended for anal use. Further, the insert 10 need not have end caps, or one or both of the end caps could be conductive. There may be various other modifications and changes to these embodiments which are within the scope of the invention.

I claim:

1. A body cavity insert for transmitting electrical energy between a body cavity wall and an electrical device, comprising:

(a) a tubular body elongated along a longitudinal axis and having a plurality of tubular segments connected end-to-end along the longitudinal axis, the plurality of tubular segments including a first conductive segment and a second conductive segment separated by a nonconductive segment;

(b) wherein the first conductive segment and the nonconductive segment have ends providing a lug-into-groove, snap-fit interlocking structure which connects the first conductive segment and the nonconductive segment end-to-end; and (c) a pair of leads in conductive communication with the conductive segments for communication with the electrical device.

2. A body cavity insert for transmitting electrical energy between a body cavity wall and an electrical device, comprising:

(a) a tubular body elongated along a longitudinal axis and having a plurality of tubular segments connected end-to-end along the longitudinal axis, the plurality of tubular segments including a first conductive segment and a second conductive segment separated by a nonconductive segment;

(b) wherein one of the first conductive segment and the nonconductive segment has a pulley-shaped end forming a groove having an outboard wall with a first diagonal edge, and the other of the first conductive segment and the nonconductive segment has a lug with a second diagonal edge, wherein the groove and the lug are formed so that the first diagonal edge and the second diagonal edge can slip past each other so that the lug snaps into the groove, thereby connecting the first conductive segment to the nonconductive segment; and (c) a pair of leads in conductive communication with the conductive segments for communication with the electrical device.

3. A body cavity insert for transmitting electrical energy between a body cavity wall and an electrical device, comprising:

(a) a tubular body elongated along a longitudinal axis and having a plurality of tubular segments connected end-to-end along the longitudinal axis, the plurality of tubular segments including a first conductive segment and a second conductive segment separated by a nonconductive segment;

(b) wherein the first conductive segment includes a conductive outer ring having an inner surface and a tubular metal base having an outer surface adjoining and in electrical communication with the inner surface of the conductive outer ring;

(c) wherein each of the conductive outer ring and the tubular metal base has a pulley shaped end structure and wherein one of the end structures has a radial projection and the other end structure has a radial groove, the projection snapping into the groove and establishing a mechanical connection and maintain electrical communication between the conductive outer ring and the tubular metal base; and (d) a pair of leads in conductive communication with the conductive segments for communication with the electrical device.

4. A body cavity insert for transmitting electrical energy between a body cavity wall and an electrical device, comprising:

(a) a tubular body elongated along a longitudinal axis and having a plurality of tubular segments connected end-to-end along the longitudinal axis, the plurality of tubular segments including a first conductive segment and a second conductive segment separated by a nonconductive segment;

(b) wherein an electrically conductive tail is formed as an integral part of the first conductive segment; and (c) a pair of leads in conductive communication with the conductive segments for communication with the electrical device, one of such leads being connected to the conductive tail.

5. A body cavity insert for transmitting electrical energy between a body cavity wall and an electrical device, comprising:

(a) a tubular body elongated along a longitudinal axis and having a plurality of tubular segments connected end-to-end along the longitudinal axis, the plurality of tubular segments including a first conductive segment and a second conductive segment separated by a nonconductive segment;

(b) wherein a substantially solid mound of conductive material is formed on the first conductive segment, the mound not being bored or otherwise adapted to facilitate insertion of a lead; and (c) a pair of leads in conductive communication with the conductive segments for communication with the electrical device, one of such leads piercing the mound so that conductive communication is established between the mound and the lead.

* * * * *